United States Patent [19]

La Forge et al.

[11] Patent Number: 4,519,043
[45] Date of Patent: May 21, 1985

[54] SOLENOID ACTIVATED CLOSURE DEVICE

[75] Inventors: David H. La Forge; Peer M. Portner, both of Kensington, Calif.

[73] Assignee: Novacor Medical Corporation, Oakland, Calif.

[21] Appl. No.: 400,027

[22] Filed: Jul. 20, 1982
(Under 37 CFR 1.47)

[51] Int. Cl.³ .......................... G01B 7/14; A61F 1/00
[52] U.S. Cl. ........................................ 364/571; 3/107;
324/207; 364/166; 364/174
[58] Field of Search ............... 364/480, 481, 570, 571, 364/563, 166, 174, 183; 310/14, 23; 318/127, 128; 3/107; 128/1 D; 324/207

[56] References Cited

U.S. PATENT DOCUMENTS 2,816,514 12/1957 Freese .
3,263,105 7/1966 Heyek .
3,308,361 3/1967 Nakai et al. .
4,355,280 10/1982 Duzich .................................. 324/207
4,384,829 5/1983 Conley et al. .......................... 3/107
4,389,737 6/1983 Robinson et al. ....................... 3/1.7
4,413,950 11/1983 Wiernicki ............................. 318/127

OTHER PUBLICATIONS

Bindels, John, *Trans. Amer. Soc. Artif. Int. Organs,* 8:140, 1962.
Bindels, J., et al., *Trans. Amer. Soc. Artif. Int. Organs,* 7:369, 1961.
Freebairn, D. et al., *Trans. Amer. Soc. Artif. Int. Organs,* 10:166, 1964.
Fuller, J. W. et al., *Trans. Amer. Soc. Artif. Int. Organs,* 14:352, 1968.
Fuller, J. W. et al., *IEEE Trans. Biomed. Eng.,* 16:184, 1969.
Portner, Peer M. et al., *7th Intersoc. Energy Conv. Eng. Conf. Proc.,* p. 784, (1972).
Jassawalla, J. S. et al., 10th Intersoc. Energy Conv. Eng. Conf., p. 1466, (1975).
Jassawalla, J. S. et al., Proc. 29th Ann. Conf. Eng. Med. Biol., p. 243, (1976).
Portner, P. M. et al., *Trans. Amer. Soc. Artif. Int. Organs,* 24:98, (1978).
Portner, Peer M. et al., *Artificial Organs,* vol. 2, No. 4, 402, (1978).
Portner, Peer M. et al., Proc. Annual Contractors Meeting, Devices and Technology Branch, NHLBI, pp. 73-74, (1978); pp. 41-42, (1979).

*Primary Examiner*—James D. Thomas
*Assistant Examiner*—Dale M. Shaw
*Attorney, Agent, or Firm*—Fitch, Even, Tabin Flannery

[57] ABSTRACT

A solenoid closure servo control eliminates impact of the solenoid poles against each other upon closure of the device. A model of the device closure is obtained from a parameter of initial gap. During closure of the device, the rate of closure of the gap of the solenoid and the force in balance between the spring and magnetic force is calculated and compared to the model. Imbalances are corrected by applying a corrective voltage to the solenoid coils.

8 Claims, 5 Drawing Figures

SOLENOID ACTIVATED CLOSURE DEVICE

The present invention relates generally to solenoid activated closure devices and more particularly to improvement in solenoid closure servo control.

Solenoid activated closure devices find a particularly useful application in the art of mechanical cardiac assist pumps. One such pump has been disclosed in U.S. patent application Ser. No. 211,210 filed Nov. 28, 1980. In the device disclosed therein, the solenoid is normally biased open by a pair of springs. The springs are operatively coupled between the solenoid and the pump bladder. Upon application of a current to the solenoid, the solenoid instantaneously closes thereby generating spring force to compress the bladder.

A limitation of the disclosed device is that the solenoid upon closing generates excessive, undesirable impact energies when each core of the solenoid strikes against each other. Balancing of the bias spring force and terminal magnetic force of the solenoid is possible however because of the unknown initial gap of the solenoid, the terminal forces do not always balance.

It is therefore an important object of the present invention to provide a solenoid activated closure device which minimizes impact energies.

It is yet another object of the present invention to provide a solenoid activated closure device which uses servo control methods for minimizing the impact energies.

Figure 1:
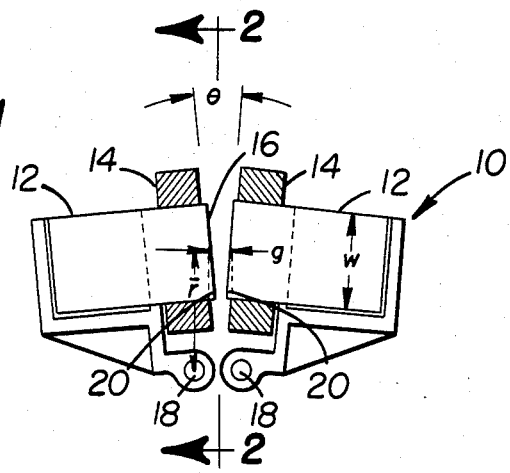
FIG. 1 shows a solenoid device particularly useful in practicing the method of the present invention.
Figure 3:
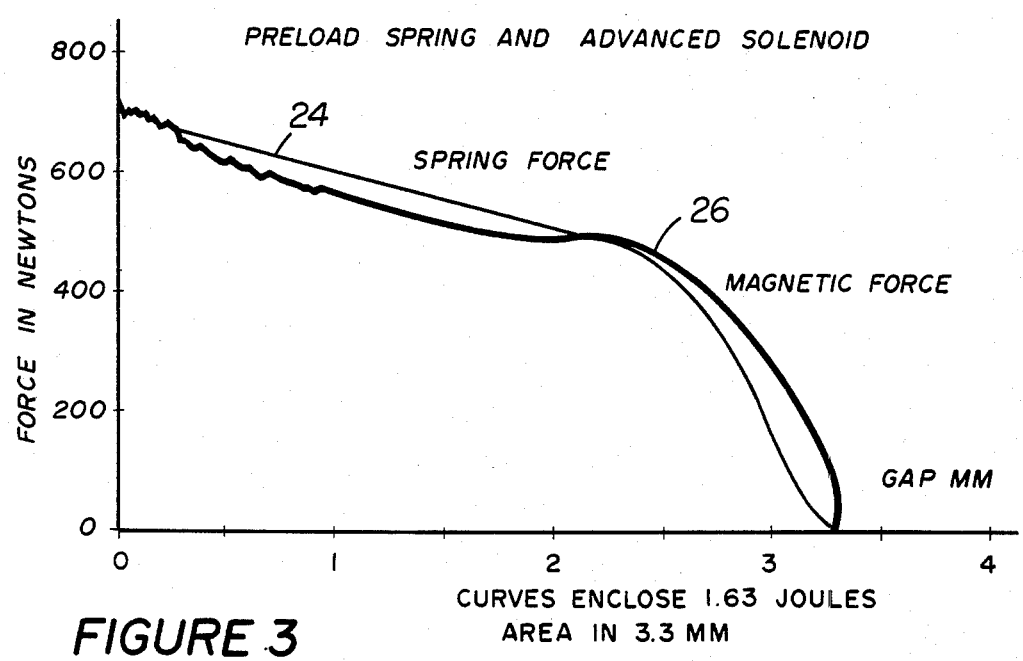

FIG. 3 diagrammatically illustrates magnetic force and spring force as a function of the gap of the solenoid shown in FIG. 1.

Figure 4:
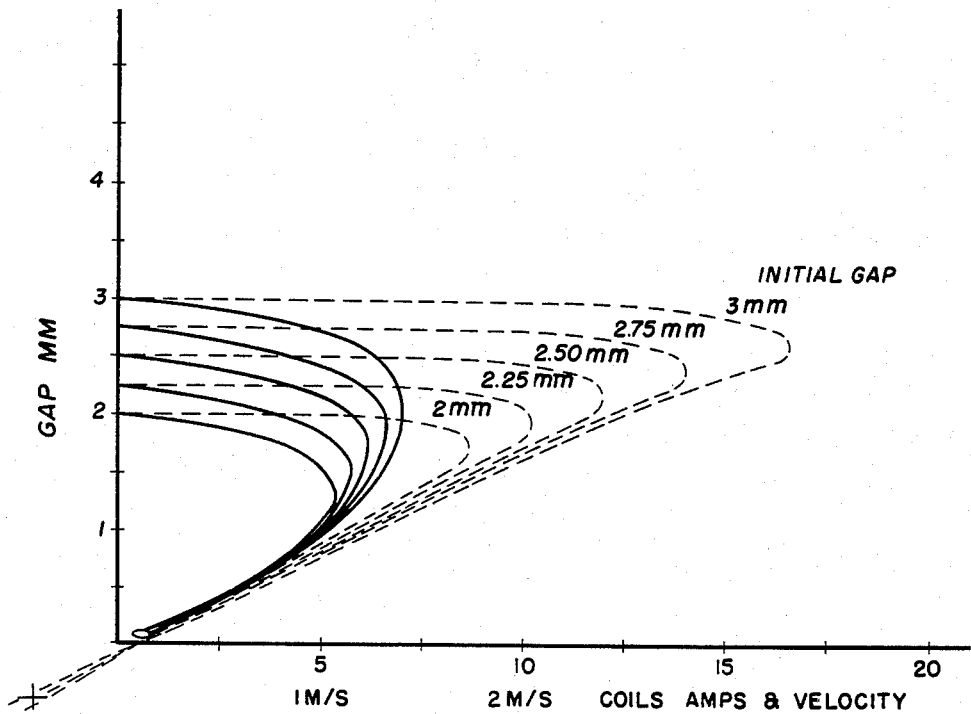
Figure 5:
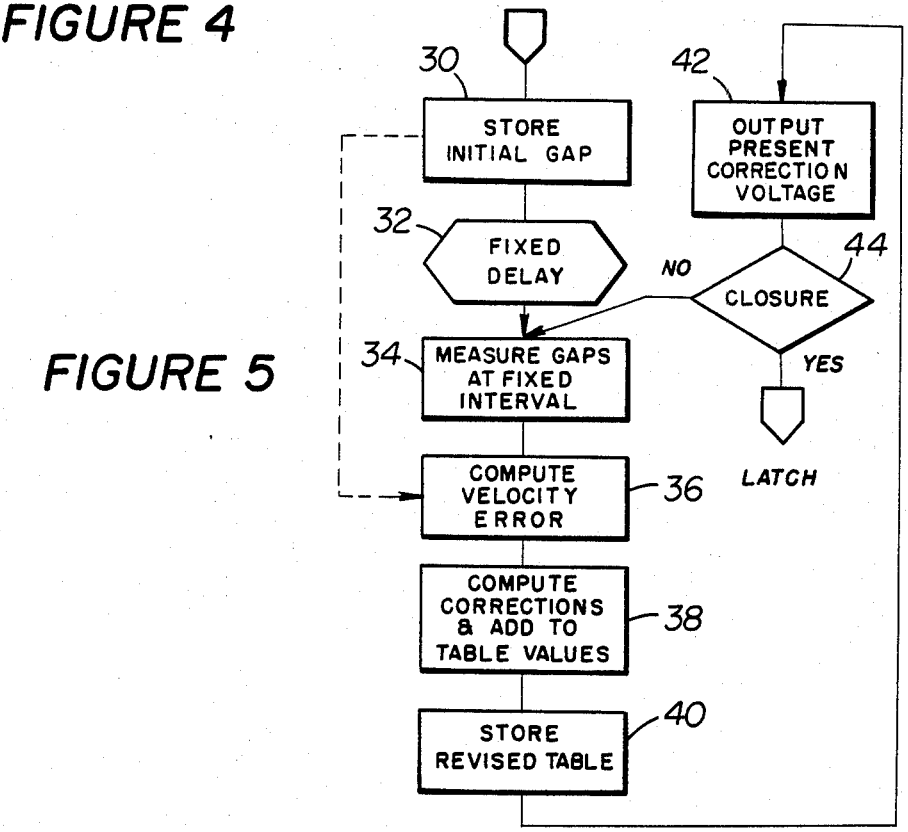

FIG. 4 diagrammatically illustrates solenoid amperage and the rate of closure of the gap as a function of gap width for the solenoid shown in FIG. 1; and FIG. 5 illustrates a flow chart illustrating the sequence of events in practicing the method of the present invention.

According to the principles of the present invention, the impact of the poles of the solenoid may be substantially eliminated by first measuring an initial width of the gap of the solenoid at the time of activation of the device and measuring the instantaneous width of the gap at selective time intervals after activation. An instantaneous rate of closure of the gap is then computed from each instantaneous width and an error is computed between the instantaneous rate in a predetermined rate of closure. The instantaneous rate of closure is then adjusted as a function of the error. The measurements of the instantaneous width and the computing of the rate of closure and the adjusting of the instantaneous rate of closure is repeated until closure of the solenoid device is determined.

Figure 2:
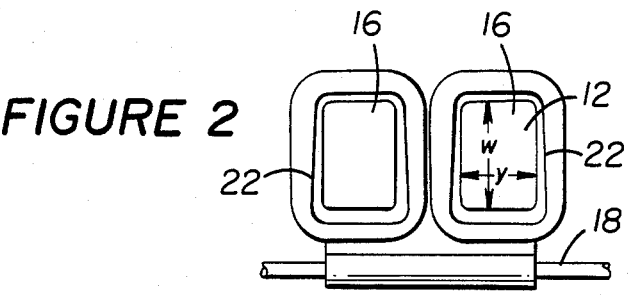
FIG. 2 is a view taken along line II—II of FIG. 1.

Describing the invention with reference to a particular embodiment thereof, FIGS. 1 and 2 show the solenoid 10 having a pair of C-shaped cores 12, and a coil 14 disposed at each end of cores 12. The end of each of cores 12 defines a pole 16 having a width w and a height y. Poles 16 are disposed in a facing relationship with each other defining a gap g.

Solenoid 10 further includes a pair of parallel axes 18, each of cores 12 being rotatably mounted on different one of axes 18. An angle 0 is defined between pole 16, gap g being measured at the midpoint of pole 16, as best seen in FIG. 1. Poles 16 are normally biased in a spaced apart relationship. Closure of solenoid 10 is initiated by a capacitive discharge which includes a current in each coil 14. A full description of solenoid 10 may be obtained from U.S. patent application Ser. No. 211,210 filed Nov. 28, 1980, the relevant parts of which are incorporated herein by reference.

A feature of the present invention is that at full gap, i.e. gap g at a maximum, and when the magnetic field intensities between poles 16 are operated slightly below saturation, a pole region 20 at the tip of each pole 16 becomes saturated. As the gap lift g decreases, saturated region 20 "travels" across pole 16 along its width w. The energy transfer of this design allows minimization of the pole area given by wxy, but achieves the same energy transfer of an equivalent pole 22 operated at saturation. Qualitatively, because gap-stored energy depends upon the square of the flux density, a non-uniform gap stores more energy for the same total flux than a uniform gap of the same volume.

Referring now to FIG. 3, in one embodiment of the present invention, the spring force diagramatically illustrated at 24 which solenoid 10 acts against is non-linear. As hereinafter described, magnetic force, illustrated at 26, is initially greater than spring force, indicating acceleration of the rate of closure of gap g, a magnetic force is then controlled to be less than spring force as the gap g decreases to deaccelerate the closure of gap g.

Referring now to FIG. 4, there are shown various representations of current (dashed lines) through coils 14 and rate of closure (solid lines) of gap g, with initial gap as a parameter. When solenoid 10 is activated by capacitive discharge, it is noted that the current peak occurs when gap g is at about roughly ⅔rds of the initial gap. The current locus, after peak current has occurred, is rectilinear and the location of the current peak with respect to gap depends on initial gap in a linear fashion. Thus, the current i may be written as a function of gap as $$i = \lambda g' \tag{1}$$

Referring to FIG. 4, graphical analysis shows that the slope lambda is given by $$\lambda = 3.6 + 0.8 g_i \tag{2}$$

depends linearly on initial gap. As best seen in FIG. 4, the intercept is not zero current at zero physical gap, since the finite permeability of the core introduces an effective "residual gap". Thus, $$g' = g + 0.08 \tag{3}$$

where g is physical gap, measured as best seen in FIG. 1.

It is known that inductance, l, of coils 14 disposed about cores 12 is given by $$l = k/g' \tag{4}$$

where k is a magnetic core constant. The voltage loop equation after capacitive discharge may then be given by $$v_s = ir + k(di/gdt - idg/g^2 dt) \tag{5}$$

Linear dependence of the current i on g implies that the applied voltage $v_s$ is equal to the mean resistive voltage drop, defining a "coast" voltage.

Known relationships of magnetic force and excitation are valid for solenoid 10 as described hereinabove, results in the equation for magnetic force $$f_{mag} = -ki^2/2g^2 \tag{6}$$

and eliminating current from equation (6) gives $$f_{mag} = -\lambda^2 k g'^2/2g^2 \tag{7}$$

Since the total gap g far exceeds the residual gap, the approximation $$g'^2/g^2 = 1 + 0.16/g \tag{8}$$

is justified and therefore $$f_{mag} = -\lambda^2 k[1 + 0.16/(g+0.08)]/2. \tag{$\approx$}$$

If velocity of solenoid 10 is mismatched from the curve shown in FIG. 4, velocity error will deviate only moderately at the peak but diverts rapidly as closure progresses leading either to misfire where solenoid does not close or to impact. However the current versus gap relationship is still substantially linear, only the slope thereof changing. In view of the magnetic force formula given in equation (7), this behaviour implies a constant force offset throughout the latter part of closure can be described as a perturbation of the constant force or $$f_{mag} = -\lambda^2 k[(1+0.6/(g+0.08)(1+2\Delta i/i)]/2; \tag{9}$$

$$\Delta f = -\lambda k \Delta i/g'. \tag{10}$$

The gap dependency is removed by substituting the inductance formula (equation 4) into equation 10 which gives $$\Delta f = -\lambda v_e \Delta t. \tag{11}$$

$v_e$ gives the error or servo correction voltage, relative to the previously defined coast voltage.

Mechanical motion of solenoid 10 may be derived from FIG. 4. In a match closure condition, i.e. when terminal velocity equals zero upon application of the appropriate pulse voltage, the magnetic force is independent of gap, therefore the characteristic motion of solenoid 10 is harmonic, governed by its intertial mass and spring force (FIG. 3). The rate of closure of gap g is then given by $$-u_{pk} = 0.43 + 0.325 g_i \tag{12}$$

and successive gap measurements may be given by $$g_u = 0.80 g_i - 0.27. \tag{13}$$

The characteristic frequency of the harmonic motion is independent of initial conditions. However effective phase of the harmonic wave relative to the time of peak velocity is affected by the initial gap g and may be given by $$\text{tau} = 0.55 + 1.0 g_i \tag{14}$$

Thus for all times after the first 1.35 milliseconds, the equations of motion are $$g = gu[1 - t/\text{tau} - 1/\pi \sin(\pi t/\text{tau})]; \tag{15}$$

$$u = -u_{pk}/2[1 + \cosin(\pi t/\text{tau})]; \text{ and} \tag{16}$$

$$a = -u_{pk}(\pi/\text{tau}) \sin(\pi t/\text{tau}). \tag{17}$$

Equations 15-17 define a family of glide paths from which feedback control equations may be developed. However, the exact glide path equations need not be used. Servo control may also be based on the establishment of a system linearity about known normal characteristics which permits error-free superposition of succeeding correction actions. Thus, a correction signal can be added without invalidating previously computed corrections still in force. The harmonic character of the motion makes possible simultaneous nulling of the net force and of the velocity at zero gap since the acceleration, velocity and gap are at 90° phases.

A simplified model may be substituted for equations 15-17 and be parabolic in nature in given by $$u = -ag + bg^2; \tag{18}$$

$$a = -2u_{pk}/gu; \text{ and} \tag{19}$$

$$b = u_{pk}/g_u^2. \tag{20}$$

The coefficients a and b are defined by matching the parabola defined by equation 18 to peak velocity and passing through an origin defined by zero gap and zero velocity. Thus equations 18-20 are functions only of system constants and initial gap.

To determine the magnitude of correction signals required, it is necessary to estimate the time remaining for corrective action to take place. The quadratic form of the velocity-gap relationship leads to $$\Delta t = (g/c)^{\frac{1}{2}}, \tag{21}$$

where the constant is derived from the previously established glide distance and time $$c = g_u/\text{tau}^2. \tag{22}$$

Referring now to FIG. 5 there is shown a flow chart for the servo algorithm incorporating the above described relationships and equations. The first step of the servo method is to measure and store the initial gap of solenoid 10, indicated at 30. As indicated at 32, the method includes a fixed delay calculated commensurately as hereinabove described to allow the rate of closure of gap g to reach a maximum. After the rate of closure of gap g has reached a maximum, the instantaneous gap, $g_u$, may be measured at fixed time intervals as indicated at 34. From the instantaneous gap measured at fixed time intervals, the rate of closure, $U_{pk}$, of gap g may also be computed. Indicated at 36 it is seen that the instantaneous rate of closure is compared to the model values given in equations 17-19 or 20-22. From this comparison a velocity error may be calculated which is the difference between the instantaneous rate of closure and the predicted rate of closure given by the model.

Indicated at 38 is indicated that the corrections from the velocity error are computed and added to the model hereinabove described. If no velocity error was computed at 36, the computing method at 38 includes reading the current through coil 14, and computing a force imbalance, Δf, that exists during closure. This force imbalance is added algebraically as $$\Delta f = m\Delta u/t. \quad (23)$$

A force error is then determined and the appropriate coast voltage is set therefrom.

If at 36 there is a velocity error computed, such error is computed with the last such velocity error in the prior cycle. If the velocity error is not worse than the prior cycle, the method includes estimating the time to close solenoid 10, and computing a corrective force given by $f = m\Delta u/t$. The method then includes the steps as if no velocity error was present.

If the velocity error is worse than the prior cycle, a determination is made whether such error is higher or lower than the prior cycle.

Indicated at 40, it is indicated that the corrections hereinabove described are stored.

Indicated at 42, the necessary corrections are outputted as voltage, either the coast voltage, or a dump or a boost voltage. The dump or boost voltage is applied whenever the velocity error is worse than a prior cycle or a force error exists when there is no velocity error.

At 44 it is indicated that a determination is made if solenoid 10 has closed i.e. gap g at zero. If there is no closure, the steps of the method commensing at 34 are repeated. If there is a closure, the method further includes computing of force and balance between the magnetic latching force and the spring force at closure. If there is sufficient latch force, the method terminates. If there is an insufficient latch force, i.e., spring force greater than magnetic force, a snare pulse is applied to solenoid 10 and more particularly coil 16 to insure latching of the device.

Various modifications of the invention in addition to those shown and described herein will become apparent to those skilled in the art from the foregoing description and accompanying drawings. Such modifications are intended to fall within the scope of the appended claims.

What is claimed is:

1. In a solenoid activated closure device having a pair of poles in a facing relationship to each other and normally biased apart from each other defining a gap therebetween, said poles being accelerated toward each other when said device is activated, a method for substantially eliminating impact of said poles against each other after activation of said device, said method comprising the steps of:
   a. measuring an initial width of said gap;
   b. measuring an instantaneous width of said gap at selected time intervals after activation of said device;
   c. computing an instantaneous rate of closure of said gap from each instantaneous width and computing an error between each instantaneous rate and a predetermined rate of closure;
   d. adjusting said instantaneous rate as a function of said error; and
   e. repeating steps b-d until closure of said device is determined.

2. In a solenoid activated closure device having a pair of poles in a facing relationship to each other and normally biased apart from each other defining a gap therebetween, a method for optimizing energy transfer of said device when activated comprising:
   pivotably mounting each of said poles whereby said gap is non-uniform when said poles are biased apart from each other;
   energizing said device with a current selected to limit initially a saturation region of said poles to a first pole tip region thereof, said saturation region transversing said poles during closure of said gap, said saturation region increasing gap-stored energy enhancing effective cross-sectional area of said poles defining an equivalent non-saturating virtual pole of greater cross-sectional area than each of said poles.

3. A method in accordance with claim 1 wherein said computing step further includes repeatedly computing said error and comparing each computed error with the immediately preceding computed error, and superimposing a predetermined incremental amount of energy upon said energy applied to said solenoid whenever said computed error is greater in magnitude than the immediately preceded computed error.

4. A method in accordance with claim 3 wherein said incremental amount of energy lessens the total energy applied to said solenoid when said velocity error indicates that said solenoid has a higher velocity than the predetermined velocity.

5. A method in accordance with claim 3 wherein said incremental amount of energy increases the total energy applied to said solenoid whenever said velocity error indicates said solenoid has a velocity less than said predetermined velocity.

6. A method in accordance with claim 1 which further includes computing a force imbalance between the magnetic latching force and a spring force acting in opposition to said magnetic force when said solenoid has closed.

7. A method in accordance with claim 2 wherein said saturation region at said first pulse tip region develope a fringing field outside of the cross-sectional area of said pulse, said fringing field effectively linearizing the magnetic force developed between said poles.

8. A method in accordance with claim 2 wherein said non-uniform gap further increases magnetic stored energy further enhancing effective cross-sectional area of said pulse.

* * * * *